United States Patent [19]

Williams

[11] 4,049,000

[45] Sept. 20, 1977

[54] SUCTION RETRACTION INSTRUMENT

[76] Inventor: Robert W. Williams, 3201 Maryland Parkway, Las Vegas, Nev. 89109

[21] Appl. No.: 601,058

[22] Filed: Aug. 1, 1975

[51] Int. Cl.² ............................................. A61M 1/06
[52] U.S. Cl. .................................... 128/276; 128/20; 32/33
[58] Field of Search ................... 128/276, 278, 11.12, 128/20, 343, 276, 350 R, 20; 32/33

[56] References Cited

U.S. PATENT DOCUMENTS

| 1,167,062 | 1/1916 | Groshans | 32/33 |
| 1,621,212 | 3/1927 | Myers | 128/276 X |
| 3,460,255 | 8/1969 | Hutson | 32/33 |
| 3,557,456 | 1/1971 | Hutchinson | 32/33 |
| 3,626,471 | 12/1971 | Florin | 128/276 X |
| 3,965,901 | 6/1976 | Penny | 128/350 R |

FOREIGN PATENT DOCUMENTS 823,933  9/1969  Canada .................................. 128/276

Primary Examiner—Louis G. Mancene
Assistant Examiner—Wenceslao J. Contreras
Attorney, Agent, or Firm—Jerry R. Seiler

[57] ABSTRACT

A suction retraction instrument comprises an elongated hollow suction pipe having a port at its lower end and secured to a manifold at its upper end and a retractor arm secured to the pipe adjacent the lower end and extending at an angle therefrom.

12 Claims, 6 Drawing Figures

SUCTION RETRACTION INSTRUMENT

BACKGROUND OF THE INVENTION

A use of a suction instrument in order to remove fluids from the immediate area in which surgery is being performed is well established. One such instrument widely used comprises a device connected to a suction pipe secured at its upper end to a holding block having an orifice on its upper surface which communicates with a passageway extending through the block from the suction pipe. The orifice allows the surgeon or operator to control suction selectively using a finger to occlude the orifice. Closing the orifice results in full suction at a port on the lower pipe end while opening the orifice will relieve the vacuum along the pipe. Although such a device gives adequate control of selective intermittent suction and removal of fluid, because of the positioning of the orifice on the block it cannot be conveniently cleaned. For example, often tissue or other solid materials are drawn into the suction pipe which then must be removed by passing a wire or cleaning rod through the suction pipe in order to force out the material. However, during this cleaning procedure material is often forced into the orifice and with a very short passageway extending into the blocked passageway at a right angle, it is most difficult to clean.

In certain surgical techniques, especially in microlumbar discectomy, it is desirable to utilize a retractor or a retraction instrument in order to displace vessels or nerves from their normal positions during the procedure. Such nerve or vessel displacement is especially desirable during surgery when they might otherwise lie in a position and mask or interfere with the field view of the surgeon during the micro-surgery. Moreover, where the vessel or nerve normally lies immediately adjacent material to be removed during the surgery, there is always the danger of injury to the nerve or vessel.

SUMMARY OF THE INVENTION

It is the object of the present invention to provide an improved suction instrument which may be easily and conveniently cleaned. It is also an object to provide an improved suction instrument having a suction control or release orifice in a position convenient for intermittent occlusion. It is another object to provide a suction control orifice and passageway of a size sufficient to release substantially all suction from the suction tip of the instrument when the control orifice is open. It is a further object to provide a suction instrument having a retractor arm. It is still a further object to provide a suction instrument having means for reducing the amount of solid tissue or material which may otherwise enter into the device which could otherwise cause plugging thereof and interrupt its effectiveness. It is yet another object to provide an instrument having improved structural characteristics. These objects will be more evident from the following detailed description.

DETAILED DESCRIPTION OF THE INVENTION

Figure 1:
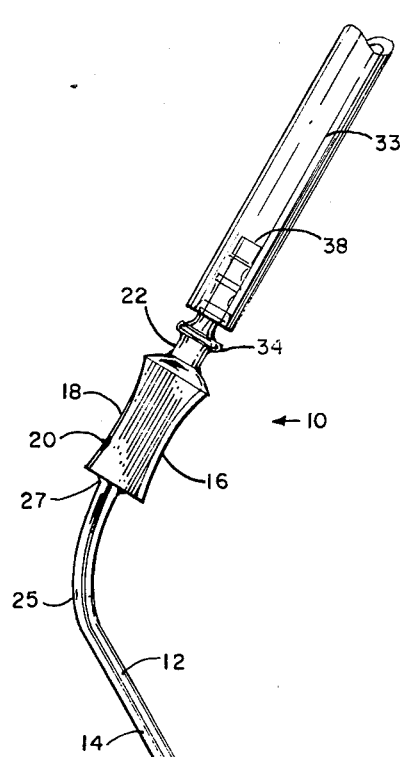
FIG. 1 is a side elevational view of the improved suction retraction instrument of the invention.

FIG. 1 shows a preferred embodiment of the suction retraction instrument of the invention 10 having an elongated hollow suction pipe 14 extending between a lower suction and 28 and upper end 27 which is secured to manifold 16. Suction pipe 14 has a major lower straight portion 21 and an upper curved portion 25 although the specific length of the pipe as well as its portions are not especially critical and will depend on ay desirable instrument design.

Figure 2:
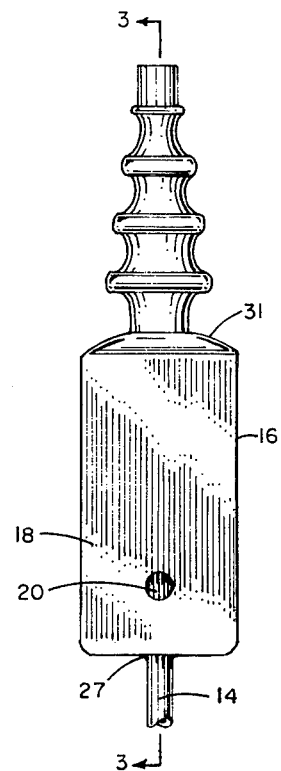
FIG. 2 is a top view of a portion of the instrument of FIG. 1 showing an improved manifold.
Figure 3:
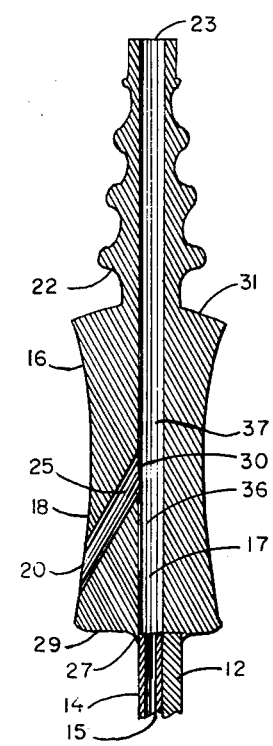
FIG. 3 is an enlarged section elevational view taken along lines 3—3 of FIG. 2.

Manifold 16 is shown in FIGS. 2 and 3 and has a forward end 29 from which pipe 14 extends and is secured, and rear end 31 preferably having an end member 22 for being connected to a suction tube or hose 33. The connecting member has a passageway 22 communicating with the passageways in manifold 16. Accordingly, the connecting member and manifold may be formed as an integral unit. When the instrument is attached to a suction tube or hose 33 connected to a vacuum source, a vacuum will be pulled through the instrument from suction end 28 of pipe 14 and orifice 20 on the manifold. The connecting member 22 preferably includes a plurality of ring shaped ribs for attachment to suction tube 33. It may be preferred to use rings or increasing diameters from connecting member end 38 so that the instrument may be secured to different diameter suction hoses or tubes. Such a feature as well as equivalent means for so attaching the device will be understood by those skilled in the art.

A significant improvement of the instrument of the invention over previously known suction devices of this type is in the design of the manifold 16. As shown in FIGS. 2 and 3 a main or first passageway 17 extends through the manifold from its forward end 29 to its rear end 31 where it communicates with hollow interior 23 of the connecting member. A second passageway 25 meets first passageway 17 at junction 30 interiorly of the manifold with the second passageway terminating at orifice 20 located on top manifold surface 18. Both passageways are preferably straight for convenient cleaning. Thus, the first passageway may be cleaned by passing a wire or cleaning rod from either end 28 or 38 to the other end while the second passageway is cleaned from orifice 20, along the passageway and on through the connecting member to its end 38.

Noting particularly FIG. 3, second passageway 25 meets first passageway 17 at junction 30, so that the first passageway has a forward portion 36 extending from the junction to the forward end 29 of the manifold and a rear portion 37 extending from the junction to end 31. Preferably the second passageway 25 forms an acute angle with the forward first passageway portion 36. The angle is preferably less than 45° and more preferably is between about 15° and 40°. Suction at end 28 of pipe 14 is normally controlled or selected by the surgeon placing a finger over orifice 20 which provides full suction to be drawn along the pipe. Accordingly, as the device is used, suction can be intermittently achieved when it is desired to remove fluid during a surgical procedure with suction end 28 extending into the area at which the fluid is present. Since this intermittent suction is controlled by the surgeon's finger at the control orifice 20, the orifice and passageways 25 and 17 are preferably of a larger bore or cross-section than that of passageway 15 in pipe 14. The purpose of this feature is so that when orifice 20 is open, substantially no suction will be pulled from suction end 28 of the pipe but instead through second passageway 25. If the manifold passageway were of substantially the same bore or diameter as that of the pipe, even with orifice 20 open some suction would be drawn through the pipe and suction end 28 which may be undesirable at any given time during a surgical procedure. However, with the manifold passageways and orifice 20 sizes or diameters greater than the hollow pipe interior diameter, opening of the orifice will cause substantially all suction to be drawn therethrough thereby fully relieving any pull through the pipe. Preferably the manifold passageway and orifice have diameters of at least 1½ times to 2 times that of the interior passageway 15 of pipe 14 as shown in FIG. 3. It is also considered that the increased flow of gas in the manifold as port 20 is intermittently opened and closed will also assist in cleaning the manifold passageways by preventing particles from settling or building up therein. Moreover, with forward manifold passageway 36 so enlarged, there will be no substantial Bernoulli effect in that portion when suction is relieved by opening port 20.

Again, convenience and ease in cleaning the device is an important improvement so that when a cleaning rod or similar device is pushed from suction end 28 of pipe 14, it will force any tissue or other materials through the instrument without normally causing it to be clogged in passageway 25. However, if some of the material does move into the upper passageway from junction 30, this may be removed by simply passing the cleaning rod through orifice 20, passageways 25 and 37 and on through the instrument. The smaller the acute angle between forward passageway portion 36 and second passageway 25, the less bending of the cleaning rod will be required during the cleaning procedure.

Figures 4, 5:
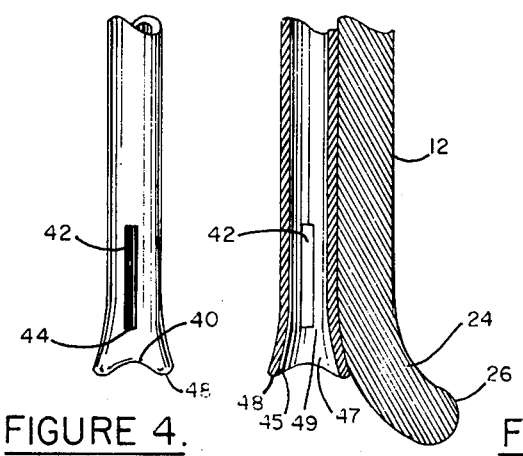
FIG. 4 is an enlarged view of an improved suction tip embodiment.
FIG. 5 is a sectional view of the suction tip shown in FIG. 4 and a retraction arm.

In another preferred embodiment of the invention the instrument is provided with a retractor 24 attached or secured to suction pipe 14 adjacent lower suction end 28 as illustrated in FIGS. 1 and 5. The retractor provides a means for using the device to displace vessels, nerves and the like in an area from which fluid is being removed during a surgical procedure. The retractor preferably extends at an obtuse angle from the axis extending along straight pipe suction 21. This angle may be any angle greater than 90° but is preferably between about 110° and 140° and more preferably about 120°. In using the device, the surgeon will normally grasp the instrument with his non-dominant hand at the manifold and insert it into the surgical area with the lower straight portion 21 of pipe 14 extending upwardly, usually near vertical. With end 28 lying or resting on a surface within the surgical area, when a vessel, nerve or other anatomical member is to be displaced the surgeon will pull the instrument toward him with end 28 acting as a fulcrum or pivot point so that the instrument is then tilted in a manner illustrated in FIG. 1, usually with straight pipe portion 21 at about 30° from vertical as shown. Alternatively, the instrument is pivoted about the manifold when the section end is not resting on a surface. As the instrument is tilted, retractor 24 acts as a lever to push and displace a vein, vessel or nerve upwardly as desired. The reason of specifying a critical obtuse retractor angle is to prevent the retractor from impaling or otherwise injuring the vessel or nerve which it is displacing as the instrument is tilted. For example, if the retractor extended from the staight pipe portion 21 at an angle of about 90°, the retractor would extend outwardly so that the instrument would have to be turned somewhat to even avoid a depression of a vessel by the retractor as the instrument is inserted into the surgical area. As the surgeon then tilted the instrument, the angle of the retractor would cause excessive displacement of the vessel or that control may be difficult.

In addition to the preferred angle at which the retractor extends, it is also preferred that lower end 26 extends substantially the same length as end 28 of pipe 14 when the instrument is held with straight pipe portion at about 30° from vertical. In other words, end 26 preferably terminates directly across from or on the same horizontal plane extending from the lowest extremity of suction end 28 when straight lower pipe portion 21 is tilted at 30° from vertical. The overall length of the retractor 24 from the point at which it begins to angle from the plane extending along the lower pipe portion 21 will depend on the specific angle thereof within the range previously described.

As further shown in FIG. 1, still another preferred embodiment includes a reinforcing member or arm 12 extending along and secured to at least a portion of the length of pipe 14. Such a reinforcing member will obviate a problem with known suction devices of this type which are quite fragile and often bend during use in certain surgical procedures. Especially in a device of the invention incorporating a retractor, where a surgeon pulls in instrument toward him with end 28 acting as the fulcrum of the instrument, where pressure is applied against less flexible anatomical members with retractor 24, pipe 14 may become bent or even broken, especially where it is of a rather small size having rather thin pipe walls. In order to avoid such a problem, the preferred instrument incorporates a reinforcing member 12, and preferably one which extends the entire length of pipe 14 having an upper end which may be secured to the forward end 29 of the manifold as shown. Moreover, reinforcing member 12 and retractor 24 may comprise a single or unitary rod-like structure with the major rod portion secured along pipe 14 and having a substantially identical or similar shape retractor 24 simply being angled therefrom at the lower end. Further, the retractor preferably has a somewhat rounded or blunted end 26 so that no sharp edges will be exposed which could cause injury to tissue, vessels or the like.

In still another embodiment a plurality of suction ports 42 are provided adjacent end 28 of suction pipe 14. Such ports preferably are elongated slots spaced upwardly along a portion of the length of the pipe from the suction end in a manner shown in FIGS. 4 and 5 and provide additional openings through which fluid may be removed from the surgical area. Because of the elongated shape of the ports, they will not normally become clogged or occluded with tissue or other particuate matter. Even where part of a port is occluded, there will be a portion open through which liquid may be directed.

Figure 6:
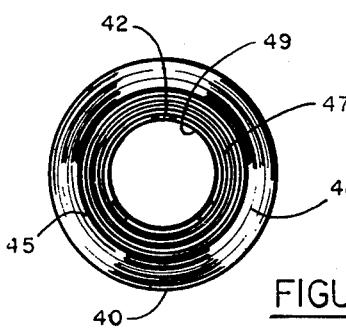
FIG. 6 is an enlarged end view of the suction tip shown in FIG. 4.

The preferred suction end embodiment also includes an expanded or flared opening having a shape and features shown in FIGS. 4–6 including an outer lip 48 having a plurality of clefts or notches 40 therealong. The notches extends upwardly for a short distance from the lip to form openings when the lip lies flat on a surface. These notches will thus prevent the lip from fully seating on a flat surface when suction is being applied fully at the suction end which could otherwise cause injury to delicate tissue membranes. At the same time when the end is lying flat on a surface, liquid may still be drawn through the notches. The number of notches is not critical and two or more, three being shown may be used. Neither is the notch size critical so long as the desired result is achieved.

The diameter of lip 48 is greater than the diameter of port 49 of the suction pipe. Preferably, the lip is rounded at least somewhat to avoid sharp or squared edges. There is also a cavity 47 formed between the inner lip orifice 45 and port 49. The elongated slot embodiment may or may not be used with the expanded and notched opening embodiment. However, when both are used the lower slot end preferably terminates at port 49 as is shown in FIGS. 5 and 6. It will be appreciated that this combination of features offers distinct advantages over previously known suction devices or instruments as will be understood by those skilled in the art.

I claim:

1. A suction retraction instrument comprising:
   an elongated hollow suction pipe having a suction port at its lower end and secured to a manifold at its upper end and having a straight lower portion extending along an axis, and
   a unitary support rod and retractor arm secured along the length of said suction pipe, the retractor arm comprising the lower end of said support rod, and wherein said retractor arm extends beyond the lower end of said suction pipe and at an obtuse angle from said axis.
2. The instrument of claim 1 wherein said angle is between about 110° and about 140°.
3. The instrument of claim 1 wherein said lower pipe portion includes a plurality of elongated slots therealong upwardly from said suction port.
4. The instrument of claim 3 wherein said lower pipe end comprises an annular flared lip extending downwardly from said port.
5. The instrument of claim 4 wherein said slots have a lower end terminating at said port.
6. The instrument of claim 1 wherein said lower pipe end comprises an annular lip having a diameter greater than the distance across said port said port being elevated above said lip.
7. The instrument of claim 1 wherein said manifold comprises a solid block member having a substantially straight first passageway extending therethrough and communicating with said hollow pipe, and a second passageway joining said first passageway interiorly of said manifold at an acute angle and communicating with an orifice on an upper manifold surface.
8. The instrument of claim 7 wherein said first and second passageway have a cross-section larger than the cross-section of the interior of said hollow section pipe.
9. The instrument of claim 7 wherein said first and second passageways have a cross-section at least 1½ times the cross-section of said pipe interior.
10. The instrument of claim 7 wherein said second passageway is substantially straight and wherein said acute angle is less than about 45°.
11. The instrument of claim 7 wherein said manifold has a forward surface to which said suction pipe is secured, said first passageway having a forward portion extending from the junction of said second passageway and a rearward portion extending rearwardly from said junction and wherein the angle between forward first passageway portion and said second passageway is less than about 30°.
12. The instrument of claim 11 including a connecting member secured to said manifold opposite said forward surface and having a conduit therein communicating exteriorly thereof and with said first passageway, and means for connecting a suction tube thereto.

* * * * *